United States Patent [19]

Kuzira et al.

[11] Patent Number: 5,030,750

[45] Date of Patent: Jul. 9, 1991

[54] PROCESS FOR PREPARING DL-SERINE AND PROCESS FOR SEPARATION AND PURIFICATION OF THE SAME

[75] Inventors: Katufumi Kuzira; Masaki Odagiri; Makoto Imanari, all of Ami; Takashi Yokoi, Shiga, all of Japan

[73] Assignee: Research Association for Utilization of Light Oil, Tokyo, Japan

[21] Appl. No.: 455,150

[22] Filed: Dec. 22, 1989

[30] Foreign Application Priority Data

Feb. 3, 1988 [JP] Japan .................................. 1-25519
Dec. 27, 1988 [JP] Japan ................................ 63-329851

[51] Int. Cl.$^5$ ............................................ C07C 227/38
[52] U.S. Cl. ..................................... 562/554; 562/567
[58] Field of Search ............................... 562/554, 567

[56] References Cited

U.S. PATENT DOCUMENTS

| | | | |
|---|---|---|---|
| 3,536,726 | 10/1970 | Fink et al. ........................... | 562/567 |
| 4,304,933 | 12/1981 | Milo et al. ........................... | 562/507 |
| 4,714,767 | 12/1987 | Tanaka et al. ....................... | 562/554 |
| 4,733,009 | 3/1988 | Miyahara et al. .................... | 562/554 |

FOREIGN PATENT DOCUMENTS

| | | | |
|---|---|---|---|
| 443325 | 2/1944 | Japan ................................ | 562/567 |
| 4948528 | 12/1974 | Japan ................................ | 562/567 |
| 57-11309 | 3/1982 | Japan ................................ | 562/567 |
| 58-172352 | 10/1983 | Japan ................................ | 562/554 |
| 58-210027 | 12/1983 | Japan ................................ | 562/554 |
| 61-10542 | 1/1986 | Japan ................................ | 562/567 |
| 62-145050 | 6/1987 | Japan ................................ | 562/554 |
| 62-255452 | 11/1987 | Japan ................................ | 562/567 |

OTHER PUBLICATIONS

Chemical Ber., No. 35 (1902), pp. 3787-3805, Emil Fischer et al.
Chemical Ber., No. 39, (1906), pp. 2644-2648, Hermann Leuchs et al.
J. Biology Chem., No. 104 (1934), pp. 511-516, Max S. Dunn et al.

Primary Examiner—James H. Reamer
Attorney, Agent, or Firm—Oblon, Spivak, McClelland, Maier & Neustadt

[57] ABSTRACT

Disclosed is a process for preparing DL-serine, which comprises synthesizing DL-serine according to Strecker reaction with use of a cyan compound, ammonium chloride, ammonia and a reaction substrate comprising glycol aldehyde, wherein the Strecker reaction is carried out under the reaction conditions of:

molar ratios of the starting materials of:
  glycol aldehyde/cyan compound: more than 1.0 and not more than 1.50
  ammonium chloride/glycol aldehyde: more than 1.0 and not more than 2.0
  ammonium/cyan compound: 1.0 to 7.0
reaction temperature: 20° to 80° C.
reaction time: 15 to 120 minutes,
and the reaction product obained in hydrolyzed.

Disclosed is also a process for separation and purification of DL-serine produced in the above by subjecting the aqueous solution containing DL-serine alkali salt obtained to ion exclusion chromatography by use of a strongly acidic cation exchange resin, neutralizing the fractionated DL-serine fractions to near the isoelectric point of DL-serine and subjecting the neutralized product to ion exclusion chromatography with a strongly acidic cation exchange resin.

9 Claims, No Drawings

PROCESS FOR PREPARING DL-SERINE AND PROCESS FOR SEPARATION AND PURIFICATION OF THE SAME

BACKGROUND OF THE INVENTION

This invention relates to a process for preparing DL-serine, particularly to an industrial process for preparing DL-serine according to the Strecker reaction by use of glycol aldehyde as the reaction substrate. Further, this invention relates to a process for separation and purification of DL-serine, particularly to a process for separation and purification of DL-serine by subjecting the reaction mixture containing glycol aldehyde obtained by dehydrogenation or oxidative dehydrogenation of ethylene glycol to the Strecker reaction (Zelinsky-Stadnikoff reaction), recovering by separation of ethylene glycol from the mixture containig DL-serine obtained by hydrolysis of the reaction product obtained, and further separating inorganic salts therefrom.

Serine is an α-amino acid. L-serine is a compound useful as amino acid transfusion, and also D-serine is useful as a starting material for antibiotics. Also, serine is a compound useful as the starting material of L-tryptophan of which development is expected in an future as the additive for fodder.

As a method for synthesizing serine according to the Strecker reaction with glycol aldehyde as the reaction substrate, there has been already a report in Fischer and Leuchs: Chem. Ber., 35, 3787 (1902) that serine is obtained by use of alcoholic solution of ammonia, prussic acid and hydrochloric acid. The yield of serine by the method of said report is very low, and it is no more than confirmation of formation of serine.

As a process by use of a glycol aldehyde analogue as the starting material, Leuchs and Geiger: Chem. Ber., 39, 2644 (1906) and Dunn. Redemann and Smith: J. Biol. Chem., 104, 511 (1934) report preparation of serine by the Strecker reaction of ethoxy acetoaldehyde obtained by dehydrogenation of ethylene glycol monoethyl ether, hydrolysis with hydrogen bromide and cleavage of ethyl group, but also the yield is low and the starting material is expensive, involving also the problems such as corrosion of the reaction vessel, etc. Thus, it can hardly be said to be a production process industrially practiced.

Also, Japanese Patent Publication No. 11309/1982 discloses a process for preparing serine by use of a glycol aldehyde precursor such as monochloroethylene oxide, etc. The yield by the process in said Publication is about 50 %, and synthesis of the starting material is also cumbersome and this process is not satisfactory as production process industrially practiced.

Also, for glycol aldehyde which is the starting material for preparation of serine, there has not yet been established an industrial production process, particularly because it cannot be easily isolated and purified. Thus, the process for preparing serine according to the Strecker reaction with the use of glycol aldehyde or its related substance as the starting material is only disclosed in several literatures including the above-mentioned report.

In none of the preparation methods, detailed investigation has been done about the Strecker reaction in which various reaction factors participate, and they involve problems as production processes industrially practiced.

As described above, preparation of serine from glycol aldehyde or its analogue has been known for long time, as reported in Fisher & Leuchs, Chem. Ber., 35, 3787 (1902), Japanese Patent Publication No. 11309/1982, etc., but its examples are few, and no industrial production process has been established. This is because preparation method of glycol aldehyde itself has not yet been established. Particularly, isolation and purification of glycol aldehyde are difficult because alcohol aldehyde has such physical properties that it is soluble in water, and also high in reactivity to be thermally unstable.

As a method for separating and purifying the synthesized serine, there is the method for preparing DL-serine from glycol aldehyde triacetate in which α-amino-βhydroxypropionitrile is prepared according to the Strecker reaction, and this is hydrolyzed with hydrochloric acid [Chem. Ber., 98, 1677 (1965)], and according to this method, after concentration of the hydrochloric acid hydrolyzed mixture to dryness, the DL-serine hydrochloride is extracted with ethanol, which is then neutralized with diethylamine or ammonia. However, concentration to dryness is industrially feasible with difficulty, and entrainment of impurities of inorganic salts, etc. may be conceivable, and also DL-serine crystallized by neutralization also contains a viscous polymer, whereby filtrability is poor and also the DL-serine purity is low.

There has been also proposed a method in which α-amino-β-hydroxypropionitrile is hydrolyzed with the use of 7-fold moles or less of sodium hydroxide, and the DL-serine formed is adsorbed onto an acidic ion exchange resin (Japanese Patent Publication No. 3325/1969). However, according to this method, during adsorption of DL-serine onto the acidic ion exchange resin, a great excess of coexisting sodium ions are also adsorbed at the same time, and therefore an extremely large amount of the ion exchange resin is required and also a large amount of aqueous ammonia is also used for desorption. Thus, it cannot be said to be an economical method.

Also, in Japanese Patent Publication No. 48528/1974, there is proposed a method in which a DL-serine hydrochloride-containing solution containing an acid is concentrated, the acid is evaporated with a large excess amount of water, and thereafter the water is replaced with a large excess amount of methanol or ethanol, inorganic salts are filtered, and alcohol is recovered, and then serine is adsorbed onto an acidic ion exchange resin, followed by elution with ammonia water. However, since this method uses large amounts of water and alcohol, and also the separation and purification steps are lengthy, it can be far from industrial process.

Thus, all of the separation and purification methods of synthesized serine known in the art are cumbersome in operations and also use a large amount of aids to be little practically available as industrial separation and purification process.

On the other hand, concerning separation and purification of amino acids by use of ion exclusion chromatography, Japanese Unexamined Patent Publication No. 255452/1987 discloses an example in which the aqueous isoleucine solution prepared by the fermentation method is applied as such. However, no good result can be obtained if the above method may be applied as such to the crude aqueous serine solution in which serine salt and ionic substances such as inorganic salts, etc. and substances having no ionic characteristic such as ethylene glycol, etc. coexist.

SUMMARY OF THE INVENTION

An object of the present invention is to provide a process for producing industrially inexpensive DL-serine by subjecting glycol aldehyde as the reaction substrate for the Strecker reaction, and optionally to separation and purification.

The present inventors have intensively studied in order to accomplish the above object, and consequently found specific Strecker reaction conditions for obtaining DL-serine at high yield with the use of glycol aldehyde as the reaction substrate. Further, by subjecting the glycol aldehyde obtained by dehydrogenation or oxidative dehydrogenation of ethylene glycol as the reaction substrate without isolation and purification, it has been found that production of DL-serine is possible economically and at high yield.

More specifically, the present invention is a process for preparing DL-serine, which comprises synthesizing DL-serine according to Strecker reaction with use of starting materials of cyan compound, ammonium chloride, ammonia and a reaction substrate comprising glycol aldehyde, wherein the Strecker reaction is carried out under the reaction conditions of:
molar ratios of the starting materials of:
  glycol aldehyde/cyan compound: more than 1.0 and not more than 1.50
  ammonium chloride/glycol aldehyde: more than 1.0 and not more than 2.0
  ammonium/cyan compound: 1.0 to 7.0
reaction temperature: 20° to 80° C.
reaction time: 15 to 120 minutes,
and the reaction product obtained is hydrolyzed.

The present inventors have found that, as a preferred embodiment of the present invention, in the above-mentioned serine synthesis from ethylene glycol, the serine alkali salt obtained by hydrolysis of the Strecker reaction product with an excess amount of a strong base can be separated from ethylene glycol by ion exclusion chromatography with a strongly acidic cation exchange resin, and further that, after neutralization, inorganic salts can be separated by subjecting the neutralized product to ion exclusion chromatography by use of a strongly acidic cation exchange resin.

More specifically, the preferred embodiment of the present invention is to carry out separation and purification after production of DL-serine, which comprises subjecting the reaction mixture containing glycol aldehyde obtained by dehydrogenation or oxidative dehydrogenation of ethylene glycol to the Strecker reaction, hydrolyzing the reaction product obtained with a strong base, subjecting the aqueous solution containing serine alkali salt obtained to ion exclusion chromatography by use of a strongly acidic cation exchange resin, neutralizing the fractionated serine fractions to near the isoelectric point of serine and subjecting the neutralized product to ion exclusion chromatography with a strongly acidic cation exchange resin. The crude aqueous serine solution to be used in the above preferred embodiment of the present invention is obtained by use of a crude glycol aldehyde obtained by dehydrogenation or oxidative dehydrogenation of ethylene glycol according to the Strecker reaction and the hydrolysis reaction.

DESCRIPTION OF THE PREFERRED EMBODIMENTS

Hereinafter, the method of the present invention will be described.

Preparation of Glycol Aldehyde

The glycol aldehyde to be subjected to the Strecker reaction of the present invention may be one prepared according to any method, and is not required to be a pure product. Preferably, for example, unpurified glycol aldehyde solution obtained by dehydrogenation or oxidative dehydrogenation is also available, and by use of such unpurified glycol aldehyde as the reaction substrate, DL-serine can be economically produced.

In the above preparation, dehydrogenation of ethylene glycol which is the starting material for synthesis is carried out with a complex system catalyst comprising copper and another inorganic component, and glycol aldehyde is prepared by dehydrogenation reaction from ethylene glycol and water.

In this case, by permitting a small amount of molecular oxygen to coexist in the reaction system, glycol aldehyde can be prepared continuously at high selectivity substantially without lowering in activity of the catalyst, whereby glycol aldehyde reaction mixture at constant concentration can be always obtained.

The dehydrogenation reaction of ethylene glycol may be performed by use of a commercially available metal oxide catalyst (copper chromite catalyst, etc.) or such catalyst added with an appropriate carrier (Alundum, alumina, etc.), etc. as the catalyst, and the reaction may be carried out in a fixed catalyst bed of normal pressure or reduced pressure gas phase. The reaction temperature may differ depending on the catalyst used, etc., but the reaction is generally carried out at 200° to 500° C. Particularly, according to the process in which minute amount of molecular oxygen is permitted to coexist in carrying out the reaction of ethylene glycol and water at 180° to 400° C. by use of a complex catalyst comprising copper and another inorganic component, for example, copper and zinc oxide, there is no lowering in activity of the catalyst in the dehydrogenation reaction, and also formation of by-products is small, whereby glycol aldehyde reaction mixture with constant concentration can be always obtained preferably.

Catalyst

As the complex catalyst system of copper and another inorganic component, a mixed catalyst or carried copper catalyst comprising copper or copper oxide as the main component, combined with another inorganic oxide or metal may be used. For example, as the mixed catalyst, oxides of Cu-Zn, oxides of Cu-Cr, oxides of Cu-Mn, or oxides of Cu-Cd, etc. may be included. As the carried catalyst, catalysts having copper oxide or the above-mentioned complex type catalyst, etc. carried on pumice, diatomaceous earth, alumina, silica, asbestos or thoria, etc. may be included.

Among them, particularly Cu-Zn oxide system catalyst is preferred, which is one prepared by calcining a composition with a ratio corresponding to 0.3 to 3 parts by weight of zinc as zinc oxide per 1 part by weight of copper as calculated on copper oxide at 500° to 1200° C. Ordinarily, the catalyst is reduced with hydrogen at a temperature of about 150° to 300° C. before used for the reaction, but without hydrogen reduction, the catalyst is rapidly reduced at the initial stage of the reaction and therefore no hydrogen reduction treatment may be performed.

REACTION CONDITIONS

By introducing ethylene glycol and water, and in addition thereto, fine amount of oxygen into the reactor filled with the above catalyst, glycol aldehyde can be produced stably for a long time. The amount of water added may be generally 0.1 to 100 mole, preferably 0.5 to 50 mole, particularly 1 to 10 mole, per mole of ethylene glycol.

Oxygen is introduced as molecular oxygen, generally as air. The amount of oxygen added may be generally 0.3 to 0.001 mole, preferably 0.2 to 0.005 mole, per mole of ethylene glycol.

The reaction temperature may be generally 180° to 400° C., preferably 200° to 350° C., particularly 240° to 290° C. At a temperature lower than 180 C, conversion of ethylene glycol is lower, while if it exceeds 400° C., selectivity of glycol aldehyde will be lowered.

LHSV may be generally 0.05 to 20/hr, preferably about 0.1 to 10/hr.

The pressure of the reaction may be either normal, reduced or pressurized. In view of economy of the reaction reactor and easiness of running, normal pressure is preferably used. As the atmospheric gas, in addition to ethylene glycol, steam and air, an inert gas such as nitrogen, argon, etc. may be also added.

PREPARATION OF DL-SERINE

STRECKER REACTION

The glycol aldehyde reaction mixture obtained in the above reaction is subjected as such to the Strecker reaction with addition of a cyan compound, ammonium chloride and ammonia.

There can be seen no great notable effect of unreacted ethylene glycol on the Strecker reaction conditions of the present invention, and it may be considered that there is substantially no participation of ethylene glycol in the Strecker reaction by use of glycol aldehyde as the substrate.

The glycol aldehyde concentration in the Strecker reaction mixture should be preferably controlled to at least 2.0% by weight, and if the concentration is lower than this level, serine yield will be lowered, As the cyan compound to be provided for the reaction, for example, sodium cyanide, potassium cyanide, etc. may be employed. Unreacted cyan compounds are decomposed in the hydrolysis step, and it may be conceivable that toxic prussic acid gas may be generated during that process, or may be also entrained into discharged water, etc. when not partially decomposed. Also, serine yield has been confirmed to be improved when slightly excess amount of glycol aldehyde to the cyan compound is used. For the reasons as mentioned above, it is preferable to use glycol aldehyde in an amount slightly in excess over the cyan compound. The molar ratio of glycol aldehyde/cyan compound to be used in the reaction may be in the range of more than 1.0 and not more than 1.50, preferably more than 1.0 and not more than 1.30.

Ammonium chloride should be preferably used in an amount in slight excess over glycol aldehyde, and the amount of ammonium chloride used may be suitably in the range of more than 1.0 and not more than 2.0, preferably more than 1.0 and not more than 1.50 in molar ratio to glycol aldehyde.

The amount of ammonia used, which is also concerned with the amount of ammonium chloride used, may be preferably used at a ratio equimolar to 7-fold moles relative to glycol aldehyde.

The solvent to be used for the reaction may be water, and it is not particularly required to add a lower alcohol such as methanol, etc.

The reaction temperature is 20° to 80° C., and at a lower temperature than this range, the progress of the reaction is slow, while at a higher temperature, glycine which is a by-product will be increase in amount.

The reaction time should be preferably made relatively short as 15 to 120 minutes, and the reaction for longer time than is necessary will increase by-products such as glycine, etc., resulting in lowered yield of serine.

For the hydrolysis reaction of α-amino-β-hydroxy-propio-nitrile synthesized according to the reaction conditions as described above, an alkali, preferably strong base, is used, and the reaction can proceed substantially quantitatively by heating at 60° to 100° C. for 3 to 5 hours to give DL-serine which is the desired product. The amount of the alkali used for the hydrolysis reaction is concerned with the amount of ammonium chloride, ammonia employed, but as a general rule should be preferably used in excess of about 1.1 to 3-fold of the theoretical amount.

According to the process of the present invention as described in detail above, production of DL-serine at high yield is possible, and by use of inexpensive ethylene glycol as the starting material, DL-serine can be produced economically.

Separation and Purification of DL-Serine

RECOVERY OF AMMONIA

After the hydrolysis reaction with use of alkali, the ammonia existing in the resulting mixture is recovered by heating. In this occasion, in viewpoint of stability and recovery efficiency of the serine, the heating should preferably be carried out under reduced pressure and the temperature should preferably be not so high. The heating temperature is, depending on the heating time, desirably in the range of 40° to 80 ° C. The recovered ammonia can be used again for Strecker reaction.

Ion Exclusion Chromatography (1)

As the intervening impurities in the aqueous serine alkali salt solution obtained in the above process, ethylene glycol and inorganic salts such as sodium chloride, etc. may be mentioned.

The aqueous serine alkali salt solution obtained as described above is subjected to ion exclusion chromatography by use of a strongly acidic cation exchange resin.

In general, nonelectrolytic or weakly electrolytic compounds have been known to be separated from strongly electrolytic compounds by ion exclusion chromatography. This has been explained because strongly electrolytic compounds are excluded by Donnan potential due to ion exchange groups having charges and therefore cannot be penetrated internally of the ion exchange resin, while nonelectrolytic or weakly electrolytic compounds can penetrate freely thereinto.

Accordingly, by subjecting the aqueous serine alkali salt solution before neutralization to ion exclusion chromatography, the serine alkali salt can be separated from nonelectrolytic ethylene glycol.

The cation exchange resin is made the form of the cation which is the counter ion of the anion existing in the solution to be treated. For example, when hydrolysis is carried out with NaOH and serine sodium salt and NaCl as the inorganic salt coexist, it is used in the form of sodium salt.

In this connection, when plural kinds of cations are contained in the solution to be subjected to ion exclusion chromatography, separation efficiency is lowered. Accordingly, for avoiding lowering in separation efficiently, it is preferable to perform pretreatment previously by way of ion exchange with cation exchange resin, etc. to remove intervening cations.

The strongly cation exchange resin to be used in the present invention may include primarily styrene type resins such as Diaion SK-102, SK-104, SK-106, SK-1B, SK-104S and SK-1BS (manufactured by Mitsubishi Kasei K.K.), XFS-43279, XFS-43280, XFS-43281, HCR-W2 and TG8500A (manufactured by Dow Chemical), C-20, C-25D, ES-26 and C-3 (manufactured by Duorite), S-100, S-109, SP-112, SP-120 (manufactured by Rebatit), IR-116, IR-118, IR-120B, IR-122, IR-124, IR-252 and IR-200C (manufactured by Amberlite), etc.

In the process of the present invention, first under the state of the serine alkali salt hydrolyzed with excessive base, ion exclusion chromatography is performed by use of a strongly acidic cation exchange resin. The treatment conditions are not particularly limited, but the amount of the ion exchange resin used may be about 1.0 to 100 ml per 1 g of the aqueous solution of serine alkali salt, and the space velocity of the developing solution should be appropriately SV =0.1 to 5.0/hr, and the temperature 10° to 80° C.

The treatment pressure may be either pressurized, normal or reduced, but in view of reaction device and operability, it is preferable to carry out the treatment at normal pressure or around normal pressure. As the treatment method, the passing system is preferable, and there is the simulated movement bed method frequently used as the industrial method for chromatographic separation. After the aqueous serine alkali salt solution is introduced into the top of the column filled with the ion exchange resin, water is passed therethrough as the developing liquid under normal pressure or around normal pressure at a temperature of 10° to 80° C. To the effluent is connected a diffractive index detector to perform fractionation of the desired product.

Initially, inorganic salts and the serine alkali salt flow out, followed by flowing out of ethylene glycol. Thus, by taking the latter portion, ethylene glycol of the intervening impurities can be separated. The ethylene glycol recovered by separation can be reused as the starting material for synthesis of glycol aldehyde.

ACTIVATED CHARCOAL TREATMENT

The aqueous serine solution obtained as described above may be neutralized as such and subjected to ion exclusion chromatography with a strongly acidic cationic ion exchange resin, but when there are coloration and by-products, etc. by the Strecker reaction, it is preferable to remove these by-products previously by activated charcoal treatment.

Activated charcoal treatment may be either the method of batch treatment by use of powdery activated charcoal, or the continuous treatment method by filling granular activated charcoal into a column. The aqueous solution as such can be treated, and no particular heating, etc. is required.

The activated charcoal to be used may be any kind of coal type activated charcoal, coconut shell type activated charcoal, charcoal type activated charcoal, petroleum pitch type activated charcoal, etc. By performing activated charcoal treatment, the aqueous serine solution becomes substantially transparent.

The activated charcoal treatment may be also conducted after neutralization, not before neutralization.

NEUTRALIZATION

The aqueous serine alkali salt solution from which ethylene glycol has been separated is controlled in pH to near the serine isoelectric point (pH=5.70) with sulfuric acid or hydrochloric acid, etc. By neutralization, serine in the aqueous solution can be separated from strongly electrolytic inorganic salts according to ion exclusion chromatography by use of a strongly acidic cation exchange resin. Neutralization can be effected by use of any desired neutralizing agent.

Ion Exclusion Chromatography (2)

The above neutralized aqueous serine solution is subjected again to ion exclusion chromatography by use of a strongly acidic cation exchange resin for separating off inorganic salts. In this case, when the serine concentration collected by fractionation is desired to be made higher, as the pretreatment method, there may be employed the method of removing water by way of reduced pressure distillation, reverse osmosis membrane, etc. However, since the solubility of DL-serine in water is about 4 % by weight at 20° C., it is simpler in operation not to increase the concentration higher than that level.

The strongly acidic cation exchange resin to be used for separation of inorganic salts may be of the same kind as or the same as that used for separation of ethylene glycol. The treatment conditions may be also the same as the separation conditions for ethylene glycol. Also, fractionation of the desired product is performed by use of a diffractive index detector as the detector. Initially, inorganic salts flow out, followed by flowing out of serine, and therefore by taking the latter half of the effluent after completion of flowing of the inorganic salts in the former half, purified serine can be obtained.

The strongly acidic cation exchange resin used for the ion exclusion chromatography (1) can be used repeatedly for the ion exchange chromatography (2) without regeneration.

The purified aqueous serine solution obtained can be used as such or concentrated by the reduced pressure distillation method, the reverse osmosis membrane device, etc.

EXAMPLES

The present invention is described below in more detail by referring to Examples and Comparative examples.

EXAMPLE 1

Into a 50-ml three-necked flask equipped with a thermometer and a cooling pipe were charged 1.32 g (22.0 mmole) of glycol aldehyde, 0.98 g (20 mmole) of sodium cyanide, 1.29 g (24.2 mmole) of ammonium chloride, 6.8 g (100 mmole) of 25% aqueous ammonia and 7.5 g of water as the solvent, and the reaction was carried out at 60 .C for 30 minutes. Then, to carry out the hydrolysis reaction, an aqueous sodium hydroxide solution containing 2.2 g (55 mmole) of sodium hydroxide dissolved in 15 g of water was added into the Strecker reaction mixture, and the reaction was carried out at 75° C. for 4 hours.

After completion of the reaction, DL-serine was quantitated by liquid chromatography. As the result, the amount of DL-serine produced was 1.94 g and that of glycine as by-product 0.0075 g. The yields as calculated on the basis of sodium cyanide were found to be 92.2% of the theoretical amount for DL-serine, and 0.5% of the theoretical amount for glycine of the by-product.

COMPARATIVE EXAMPLE 1

In the same reaction device as in Example 1, the reaction was carried out under the same conditions as in Example 1 except for changing glycol aldehyde to 1.20 g (20 mmole) and sodium cyanide to 1.08 g (22 mmole) (molar ratio of glycol aldehyde/sodium cyanide is 0.91). After completion of the reaction, DL-serine was quantitated according to the same method as in Example 1. As the result, the amount of DL-serine formed was 1.42 g, and glycine as the by-product 0.10 g. The yields as calculated on the basis of sodium cyanide were 67.5% of the theoretical amount for DL-serine and 6.6% of the theoretical amount for glycine of the by-product.

COMPARATIVE EXAMPLE 2

In the same reaction device as in Example 1, the reaction was carried out under the same conditions as in Example 1 except for changing the amount of ammonium chloride to 0.86 g (16 mmole) (molar ratio of ammonium chloride/glycol aldehyde is 0.73). After completion of the reaction, DL-serine was quantitated according to the same method as in Example 1. As the result, the amount of DL-serine formed was 1.32 g, and glycine as the by-product 0.024 g. The yields as calculated on the basis of sodium cyanide were 62.6% of the theoretical amount for DL-serine and 1.6% of the theoretical amount for glycine of the by-product.

COMPARATIVE EXAMPLE 3

By use of the same reaction device, the same amounts of the starting materials and the aid as in Example 1, the reaction was carried out under the same conditions as in Example 1 except for changing only the reaction time to 3.0 hours. After completion of the reaction, DL-serine was quantitated according to the same method as in Example 1. As the result, the amount of DL-serine formed was 1.47 g, and glycine as the by-product 0.072 g. The yields as calculated on the basis of sodium cyanide were 69.8% of the theoretical amount for DL-serine and 4.8% of the theoretical amount for glycine of the by-product.

EXAMPLE 2

Dehydrogenation of Ethylene Glycol

A catalyst obtained by calcining a catalyst precursor with an average particle size of 2 mm, a composition of 50 parts by weight of CuO and 45 parts by weight of ZnO and a specific surface area of 31 $m^2/g$ (manufactured by Nikki Kagaku, N-211) at 1000° C. in air for 4 hours was filled in an amount corresponding to 10 ml in apparent volume into a reaction cylinder made of stainless steel with an inner diameter of 15 mm.

After steam was first passed through the reaction cylinder heated at 200° C., at LHSV: 0.5/hr for one hour, hydrogen diluted with nitrogen was passed therethrough at GHSV: 600/hr for 2 hours to obtain a copper-zinc oxide system catalyst.

Next, while maintaining the reaction cylinder at 270° C., a mixture of ethylene glycol:water = 1:6 gasified through a preheater was passed therethrough at LHSV: 5/hr, and at the same time air corresponding to 0.02 mole of oxygen amount per mole of ethylene glycol was passed.

The reaction mixture obtained was found to have a composition of 8.2% by weight of glycol aldehyde, 26.6% by weight of ethylene glycol, 1.2% by weight of formic acid and 64.0% by weight of water.

Preparation of DL-Serine

Into the same reaction device as in Example 1, 16.18 g of the above ethylene glycol dehydrogenated reaction mixture containing 1.32 g (22 mmole) of glycol aldehyde, 4.31 g (69.5 mmole) of ethylene glycol, 0.19 g (4.1 mmole) of formic acid and 10.36 g of water], 0.98 g (20 mmole) of sodium cyanide, 1.29 g (24.2 mmole) of ammonium chloride and 6.8 g (100 mmole) of 25% aqueous ammonia were charged, and the reaction was carried out under otherwise the same conditions as in Example 1. After completion of the reaction, DL-serine was quantitated according to the same method as in Example 1. As the result, the amount of DL-serine formed was 1.81 g, and glycine as the by-product 0.015 g. The yields as calculated on the basis of sodium cyanide were 86.1% of the theoretical amount for DL-serine and 1.0% of the theoretical amount for glycine of the by-product.

According to the present invention, DL-serine can be obtained at high selectivity by employing specific starting material ratios and reaction conditions in synthesizing serine from glycol aldehyde according to the Strecker reaction.

Also, according to the process of the present invention, the glycol aldehyde containing reaction product obtained by the dehydrogenation reaction of ethylene glycol can be used as such for the starting material to enable one line production of DL-serine from ethylene glycol, whereby DL-serine can be produced economically from inexpensive ethylene glycol.

EXAMPLE 3

Synthesis of DL-Serine

Dehydrogenation reaction of ethylene glycol was performed by use of a copper-zinc catalyst (manufactured by Nikki Kagaku K.K., N-211) in a fixed catalyst layer of normal pressure gas phase to obtain crude glycol aldehyde. By use of 27 g of the crude glycol aldehyde as the starting material containing 2.16 g (36 mmole) of glycol aldehyde, with addition of 1.57 g (32 mmole) of sodium cyanide, 2.14 g (40 mmole) of ammonium chloride and 7.82 g (115 mmole) of 25% aqueous ammonia, the Strecker reaction was carried out at 60 C for 0.5 hour. After the reaction, 3.5 g (88 mmole) of sodium hydroxide dissolved in 10 g of water was added to carry out the hydrolysis reaction at 80 .C for 4 hours to synthesize DL-serine sodium salt.

The ammonia existing in the hydrolysis reaction mixture was recovered by heating between 50° to 60 ° C., under reduced pressure between 30 to 100 mmHg.

In 40 g of the aqueous solution containing the serine sodium salt obtained, 3.48 g of DL-serine sodium salt, 7.14 g of ethylene glycol, 2.35 g of sodium chloride and 0.94 g of sodium hydroxide were found to be contained.

Separation and Recovery of Ethylene Glycol

A glass column with an inner diameter of 30 mm was filled with 400 ml of a Na-form strongly acidic cation exchange resin (Diaion SK-1BS manufactured by Mitsubishi Kasei K.K.) and washed with a small amount of water. After the ion exchange column was heated by circulation of hot water of 60° C., 40 g of the above aqueous DL-serine sodium salt solution was introduced into the top of the column.

Subsequently, water was passed at Sv=0.4/hr, and the desired product was fractionated by detection of the refractive index of the effluent.

As a result, after about one hour, inorganic salts and DL-serine sodium salt began to be flowed out, until completed in about 45 minutes. During this operation, 125 g of the effluent was collected. Then, flowing out of ethylene glycol began, until completed within about 30 minutes. The effluent in amount of 83 g was collected during this period.

The aqueous solutions obtained were analyzed by high performance liquid chromatography. As the result, DL-serine sodium salt was found to exist in the effluent of the former half in an amount of 3.47 g (recovery 99.7%), and ethylene glycol in the effluent of the latter half in an amount of 7.03 g (recovery 98.5%).

Separation and Purification of DL-Serine

The aqueous solution containing DL-serine sodium salt fractionated was treated with activated charcoal.

As the activated charcoal, 10 ml of granular Shirasagi KL (manufactured by Takede Chemical Industries K.K.) was filled in a column, and the aqueous DL-serine sodium salt solution obtained above was passed through the column from the upper portion under room temperature at SV=3.0/hr.

Then, pH control was effected with 10 % sulfuric acid to the DL-serine isoelectric point (pH=5.70), and again ion exclusion chromatography was conducted with a strongly acidic cation exchange resin. The same ion exchange resin as used in separation of ethylene glycol was used.

By introducing 40 g of the above-mentioned neutralized aqueous DL-serine solution (containing 0.755 g of DL-serine), fractionation of the desired product was conducted under the same treatment conditions as for separation of ethylene glycol with SV=0.4/hr and 60° C., also by use of a diffrac-tive index detector.

After about one hour, inorganic salts began to flow out until completion in about 30 minutes. During this period, 81 g of the effluent was collected. Then, DL-serine began to flow out until completion in about 40 minutes. During this period, 97 g of the effluent was collected.

When the aqueous solutions obtained were analyzed by high performance liquid chromatography, DL-serine was found in the effluent of the latter half in an amount of 0.737 g (recovery 97.6%) and not contained at all in the effluent of the former half. Purification recovery of DL-serine was extremely good as 97.3%.

The purity of the purified DL-serine obtained was 97.8%, and as impurities, in addition to 1.2% of glycine, ethylene glycol and inorganic salts, etc. were confirmed in extremely small amounts.

The process for obtaining a purified DL-serine of high purity of the present invention, as an inexpensive industrial process for producing DL-serine, is carried out by synthesizing DL-serine according to the Strecker reaction of the glycol aldehyde obtained by dehydrogenation or oxidative dehydrogenation of ethylene glycol without isolation and purification, subjecting it to ion exclusion chromatography by use of a strongly acidic cation exchange resin to remove simply intervening ethylene glycol and inorganic salts.

By the above treatment, in synthesis of DL-serine, glycol aldehyde of which separation purification is difficult can be subjected to the Strecker reaction as the starting material as such without separation purification from ethylene glycol, and also the ethylene glycol recovered in the present invention can be reused for production of glycol aldehyde.

The process for separation and purification of DL-serine of the present invention solves the problems in practicing DL-serine synthesis by use of ethylene glycol as the starting material, and enables production of inexpensive DL-serine.

We claim:

1. A process for preparing high purity DL-serine from ethylene glycol as a starting material, comprising:
   i) dehydrating or oxidatively dehydrating ethylene glycol by contacting the ethylene glycol with a copper-containing catalyst in the presence of 0.001 to 0.3 mole of oxygen per mole of ethylene glycol at a temperature in the range of about 180° C. to 400° C., thereby obtaining a reaction substrate containing glycol aldehyde and unreacted ethylene glycol;
   ii) reacting said reaction substrate containing glycol aldehyde with a cyan compound, ammonium chloride and ammonia at a mole ratio of glycol aldehyde to cyan compound of more than 1.0 to not more than 1.5, at a mole ratio of ammonium chloride to glycol aldehyde of more than 1.0 to not more than 2.0 and at mole ratio of ammonia to cyan compound of 1.0 to 7.0 for 15 to 120 minutes at 20° to 80° C., thereby forming α-amino-β-hydroxypropionitrile;
   iii) hydrolyzing said αamino-β-hydroxypropionitrile at 60° to 100° C. for 3 to 5 hours in the presence of a strong base in an aqueous medium to an alkali salt of DL-serine;
   iv) subjecting said aqueous medium containing an alkali salt of DL-serine to ion exclusion chromatography over a strongly acidic styrene based cation exchange resin, thereby separating the aqueous medium into an alkali salt of DL-serine containing fraction, an inorganic salt fraction and an ethylene glycol fraction;
   v) neutralizing the alkali salt of DL-serine fraction to near the isoelectric point of DL-serine; and
   vi) subjecting the neutralized fraction to ion exclusion chromatography over a strongly acidic styrene based cation exchange resin, thereby obtaining purified DL-serine separated from inorganic salts.

2. The process for preparing DL-serine according to claim 1, wherein, in said ion exclusion chromatography purification step, the amount of said strongly acidic cation exchange resin ranges from 1.0 to 100 ml per 1 g of the aqueous solution of DL-serine alkali salt formed during hydrolysis.

3. The process for preparing DL-serine according to claim 1, wherein the mole ratio of glycol aldehyde to cyan compound is more than 1.0 to not more than 1.30 and the mole ratio of ammonium salt to glycol aldehyde is more than 1.0 and not more than 1.5.

4. The process for preparing DL-serine according to claim 1, wherein the space velocity of developing solution for the ion exclusion chromatography purification step ranges from 0.1 to 5.0/hour at a temperature ranging from 10°–80° C.

5. The process for preparing DL-serine according to claim 1, wherein, in said ion exclusion chromatography purification step (iv), the glycol aldehyde fraction is recycled for reuse in the first step of the process.

6. The process for preparing DL-serine according to claim 1, wherein the strongly acidic cation exchange resin is styrene resin.

7. The process for preparing DL-serine according to claim 1, wherein the molar ratio of glycol aldehyde/cyan compound is more than 1.0 and not more than 1.30.

8. The process for preparing DL-serine according to claim 1, wherein the molar ratio of ammonium chloride/-glycol aldehyde is more than 1.0 and not more than 1.50.

9. The process for preparing DL-serine according to claim 1, wherein the cyan compound is sodium cyanide or potassium cyanide.

* * * * *